(12) United States Patent
Turner

(10) Patent No.: US 11,116,961 B2
(45) Date of Patent: Sep. 14, 2021

(54) SYSTEM FOR CONTROLLING BLOOD FLOW RATE IN AN EXTRACORPOREAL BLOOD OXYGENATION CIRCUIT

(71) Applicant: Spectrum Medical Ltd., Gloucester (GB)

(72) Inventor: Stephen Turner, Gloucester (GB)

(73) Assignee: Spectrum Medical Ltd., Gloucester (GB)

( * ) Notice: Subject to any disclaimer, the term of this patent is extended or adjusted under 35 U.S.C. 154(b) by 585 days.

(21) Appl. No.: 15/776,653

(22) PCT Filed: Nov. 10, 2016

(86) PCT No.: PCT/GB2016/053529
§ 371 (c)(1),
(2) Date: May 16, 2018

(87) PCT Pub. No.: WO2017/085464
PCT Pub. Date: May 26, 2017

(65) Prior Publication Data
US 2018/0344912 A1 Dec. 6, 2018

(30) Foreign Application Priority Data
Nov. 19, 2015 (GB) ..................... 1520364

(51) Int. Cl.
*A61M 1/32* (2006.01)
*A61M 60/50* (2021.01)
(Continued)

(52) U.S. Cl.
CPC .............. *A61M 60/50* (2021.01); *A61M 1/32* (2013.01); *A61M 1/3639* (2013.01);
(Continued)

(58) Field of Classification Search
CPC .............. A61M 1/1006; A61M 1/1086; A61M 1/3621; A61M 1/3663; A61M 1/3664;
(Continued)

(56) References Cited

U.S. PATENT DOCUMENTS

| 6,024,692 A | 2/2000 | Dilling |
| 2012/0130299 A1 | 5/2012 | Knott et al. |
| 2012/0273415 A1 | 11/2012 | Gerber et al. |

FOREIGN PATENT DOCUMENTS

| EP | 1 086 712 | 9/2000 |
| WO | WO 02/26286 | 4/2002 |
| WO | WO 2015/112294 | 7/2015 |

OTHER PUBLICATIONS

European Patent Office, International Search Report and Written Opinion—Application No. PCT/GB2016/053529, dated Feb. 2, 2017, 3 pages.

(Continued)

*Primary Examiner* — Kai H Weng
(74) *Attorney, Agent, or Firm* — Sunstein LLP

(57) ABSTRACT

A control system in a blood line (12) of a cardiopulmonary bypass perfusion system (1) comprises a flow sensor (26) to determine a flow value indicative of the flow rate, a controller configured to process the flow value, and an adjustable restriction (28) responsive to the controller, to reduce the flow rate in the venous blood line (12) to maintain a flow rate to the venous blood reservoir that does not exceed a restriction threshold. As the adjustable restriction (28) is responsive to the flow sensor (26), this provides a closed loop control mechanism that avoids restricting the blood line (12) of the perfusion system (1) more than intended.

15 Claims, 2 Drawing Sheets

(51) Int. Cl.
*A61M 1/36* (2006.01)
*A61M 60/205* (2021.01)
*A61M 60/279* (2021.01)

(52) U.S. Cl.
CPC ........ *A61M 1/3663* (2013.01); *A61M 1/3666* (2013.01); *A61M 60/205* (2021.01); *A61M 60/279* (2021.01); *A61M 2205/3334* (2013.01); *A61M 2230/30* (2013.01)

(58) Field of Classification Search
CPC ........ A61M 1/3666; A61M 2205/3334; A61M 2205/3569; A61M 2205/50; A61M 2210/0693
See application file for complete search history.

(56) References Cited

OTHER PUBLICATIONS

United Kingdom Intellectual Property Office, Search Report—Application No. GB 1520364.9, dated Apr. 16, 2018, 3 pages.

SYSTEM FOR CONTROLLING BLOOD FLOW RATE IN AN EXTRACORPOREAL BLOOD OXYGENATION CIRCUIT

FIELD OF THE INVENTION

The present invention relates to a blood flow control mechanism in a blood supply system. In particular, the present invention relates to a control system allowing the blood flow rate in the venous line of a blood supply system to be restricted.

BACKGROUND

Extracorporeal perfusion is a process in which blood from a patient is circulated outside the patient's body and re-oxygenated to be returned to the patient. More specifically, venous (oxygen-reduced) blood which has been removed from a patient via a venous line is oxygenated by exposure to an oxygenation gas in an oxygenator for supply via an arterial line back to the patient as arterial blood.

Extracorporeal perfusion is used to substitute heart and lung functionality during a medical procedure, such as open heart surgery or lung treatment. At the end of the medical procedure, extracorporeal perfusion is gradually terminated and the heart is allowed to take over blood circulation. If complications arise, extracorporeal perfusion may have to be resumed efficiently.

The present invention is concerned with improving the options for blood supply management in the final stages of extracorporeal perfusion.

SUMMARY OF THE INVENTION

In accordance with a first aspect of the present invention, there is provided a control system to restrict the flow rate of blood in a blood line as defined in claim 1.

In the blood line, blood is permitted to flow from an inlet towards an outlet. The control system comprises a first flow sensor configured to determine a first flow value indicative of the flow rate in the blood line, a controller configured to process the first flow value, and an adjustable restriction responsive to the controller, wherein the adjustable restriction is configured to reduce the flow rate in the blood line to maintain a flow rate that does not exceed a restriction threshold.

The restriction threshold can be regarded as a maximum flow rate threshold. This may be set as a user-defined threshold. It will be understood that the restriction threshold is set at a particular flow rate level. For instance, a typical flow rate in a perfusion system—in the absence of a restriction—may be around 5 litres per minute (lpm). In accordance with the first aspect, the restriction threshold may be set to a lower value, e.g., 2 lpm.

The first flow sensor measures the first flow value. The first flow value is representative of the actual flow rate in the blood line. The controller operates the adjustable restriction to reduce the flow rate until the first flow value, as measured by the first flow sensor, is at or below the restriction threshold of, e.g., 2 lpm.

The first flow sensor may be positioned upstream or downstream of the adjustable restriction. Even if positioned upstream, the effect of a restriction on the flow rate can be accurately measured.

An adjustable restriction responsive to a flow sensor can be regarded as a closed loop control. This provides a mechanism to maintain a pre-determined flow threshold regardless of the type of tubing or the type of restriction employed. The closed loop control reduces, and practically avoids, the risk of restricting a blood line more than intended.

Hitherto, a flow rate restriction was achieved only by manually clamping a flexible tube of a blood line. Manually clamping does not allow a flow to be reduced to a chosen, pre-determined level. For illustration purposes, it is mentioned that a flexible tube has to be squeezed considerably, e.g., by more than half of its original diameter, before an effect on the flow rate becomes noticeable. The tube would have to be squeezed further to effectively reduce the flow rate. The responsive arrangement of the invention allows the level of restriction to be adjusted when the tubing is already squeezed to some extent. Due to the closed loop control, the restriction can be adjusted to a set threshold.

Furthermore, the restriction threshold may be set to a low flow level while ensuring that a minimum flow rate is maintained. This allows low restriction thresholds to be maintained in situations in which flow must not be stopped entirely.

In embodiments, the control system is configured to determine whether or not the first flow value exceeds the restriction threshold by a pre-determined margin, and configured to effect an adjustment of the adjustable restriction to maintain the flow rate below the restriction threshold.

In embodiments, the adjustable restriction comprises a gradually actuatable occlusive device.

For instance, the gradually actuatable occlusive device may be constituted by a motorised clamp acting on a flexible tube.

In embodiments, the blood line comprises a venous line for draining blood into a reservoir. The first flow sensor is configured to determine the first flow value indicative of the venous flow rate and the adjustable restriction is configured to maintain the venous flow rate in the venous line.

Embodiments of the first aspect may be used in an extracorporeal venous line of a perfusion system. The venous line allows blood from a patient to be drained into an extracorporeal venous reservoir.

By restricting the flow rate through the venous line, the amount of blood circulating in a patient may be increased.

This functionality provides options for a better control of the extracorporeal blood supply during the end phases, or "weaning", of perfusion support. The end phases may be split into (a) initiating the end of the extracorporeal perfusion support, (b) maintaining a gradually reduced extracorporeal perfusion support to allow heart performance to be monitored, (c) if required, resuming extracorporeal perfusion, and (d) when possible, completely ceasing extracorporeal perfusion and letting the heart take over circulation.

The adjustable restriction may be positioned at an inlet of the reservoir and/or upstream of an inlet of the reservoir (in the venous line). The adjustable restriction may be configured for attachment at an inlet of the reservoir or be integral with the reservoir.

The adjustable restriction and the flow sensor may be provided as a single, integrated module. The provision of flow sensor and adjustable restriction as a single module may facilitate installation in a perfusion system.

In embodiments comprising a plurality of venous lines into the reservoir, a flow sensing arrangement capable of determining a cumulative flow value into the reservoir may be provided. The adjustable restriction may be understood as an arrangement capable of restricting the flow through each one of the one or more venous lines, to reduce the cumulative flow rate below a restriction threshold.

In embodiments, the control system is provided for use in a perfusion system comprising a pump to circulate blood from the reservoir via a main blood line towards an outlet. The pump is responsive to the controller, and the controller is configured to modulate operation of the pump to maintain the throughput towards the outlet at a pre-determined output flow rate. The control system further comprises a second flow sensor configured to determine a second flow value indicative of the flow rate in the main blood line, and the controller is configured to determine a difference between the second flow value and the pre-determined output flow rate, and to adjust pump parameters to reduce the difference.

The pump of a perfusion system may be any suitable pump, such as a peristaltic pump or roller pump, or a centrifugal pump. The pump draws blood from the reservoir and brings it to a line pressure and flow rate for subsequent administration to a patient. The blood is typically pumped through an oxygenator. Other conditions, e.g. temperature, may also be adjusted prior to administration to the patient.

The second flow sensor may be a separate sensor, e.g., downstream of the pump or downstream of the oxygenator. This allows the actual flow rate to be determined, taking into account any losses that may occur between the pump and the second flow sensor.

The second flow sensor may be constituted by an arrangement deriving the second flow value from the operational parameters of the pump. E.g., for a given setup, (e.g., pump speed, tube diameter, etc.), the revolutions, or strokes, per minute can be correlated with the output flow rate.

A single controller may be provided both to control the adjustable restriction in response to the first flow value and to control the pump parameters. Alternatively, individual controllers may be provided, one each to control the adjustable restriction and to control the pump parameters.

In embodiments, the control system is configured to allow the restriction threshold and the pre-determined output flow rate to be set independently.

The output flow rate (e.g., pump performance) and the restriction threshold (e.g., the adjustable restriction) may be controlled independently.

This provides a mechanism to better control the amount of blood in the vascular system depending on the requirements of a patient. As a simplified explanation, during the end phase of extracorporeal perfusion, blood is transferred from the venous reservoir into the patient. This may be referred to as "filling" the vascular system, whereas by "filling", it is meant that the amount of blood in the vascular system is gradually increased, while correspondingly less blood is held in the extracorporeal venous reservoir.

The restriction threshold and the pre-determined output flow rate may each be set via a respective input interface. This allows a clinician to set a restriction threshold but not alter the pre-determined output flow rate. For instance, the restriction threshold may be set to 2 lpm, and no pre-determined output flow rate may be set. Thus, the output flow rate may be governed by other clinical considerations. Likewise, a clinician may set a pre-determined output flow rate without altering the restriction threshold.

The restriction threshold and/or the pre-determined output flow rate may be changed incrementally (e.g., "Increase by 0.1 lpm" or "Reduce by 0.1 lpm"), e.g., via a user interface with "up" and "down" buttons.

The pre-determined output flow rate may be set according to clinical requirements. The output flow rate may be set via an input interface. For instance, the pre-determined output flow rate may be set to 3 lpm. If the second flow value, as measured by the second flow sensor, is above the output flow rate, the controller is configured to reduce the pump performance, until blood is pumped from the reservoir at a second flow value of 3 lpm. If the second flow value is below the output flow rate, the controller may increase the pump performance until the second flow value is determined as 3 lpm.

In embodiments, the controller is configured to adjust the pre-determined output flow rate relative to the restriction threshold.

In embodiments, the controller is configured to maintain the pre-determined output flow rate above the restriction threshold, at the restriction threshold, or below the restriction threshold.

The pre-determined output flow rate may match the restriction threshold (e.g., both may be set to 3 lpm). The pre-determined output flow rate may be set as an offset relative to the restriction threshold, e.g., 0.5 lpm above the restriction threshold. The pre-determined output flow rate may be set at a percentage relative to the restriction threshold.

If the output flow rate is set higher than the restriction threshold, blood can be supplied to a patient at a higher rate than it is allowed to be drained via the venous line. This allows the vascular system to be filled. I.e., this allows the amount of blood in the vascular system of a patient to be increased.

If the output flow rate matches the restriction threshold, blood is supplied to a patient at the same rate as it is allowed to be drained. This maintains a steady amount of blood in the vascular system. Thus, extracorporeal perfusion may circulate blood at a lower rate, whereas the heart takes over the circulation of the blood in the vascular system. For instance, while the heart is stopped during a medical procedure, extracorporeal perfusion may supply and drain blood at a rate of 5 lpm. The invention allows blood to be supplied, e.g., an output flow rate of 2 lpm, and drained at no more than 2 lpm, as set by a restriction threshold.

The provision of a steady blood supply and drainage allows the heart performance to be monitored under better defined conditions.

If the output flow rate is set lower than the restriction threshold, blood is supplied to a patient at a lower rate than it is allowed to be drained. This will decrease the amount of blood in the vascular system of a patient. This reduces the load on the heart and may be appropriate during a complication.

In embodiments, the controller is configured to adjust the restriction threshold and the output flow rate synchronously.

For instance, to promote a gradual increase in heart activity, the output flow rate and the restriction threshold may be reduced synchronously. E.g., both may be reduced from 2 lpm to 1 lpm. This provides a balanced blood supply and blood removal.

The system may be configured to receive a single input value (e.g., 2 lpm) for both the output flow rate (e.g., pump performance) and the restriction threshold (e.g., the adjustable restriction). The system may be configured to receive an input value for one of the output flow rate and the restriction threshold, and the other of the output flow rate and the restriction threshold may be adjusted correspondingly.

The output flow rate and the restriction threshold may be matched, or may differ. For instance, the output flow rate may be set to 110% of the restriction threshold. In that case, if an adjustment to the restriction threshold is made, this may cause the controller to correspondingly adjust the output flow rate (and pump performance) to 110% of the previous output flow rate.

The synchronous adjustment may be bi-directional. By "bi-directional", it is meant that the output flow rate and the restriction threshold may both be increased or both be decreased. The effect is that the extracorporeal blood supply is increased (when the output flow rate and the restriction threshold are raised) and less strain is put on the heart, or decreased, respectively, such that more heart activity is encouraged.

In embodiments, the control system is configured to receive as an input a pressure value indicative of the physiological blood pressure of a patient, and to adjust the output flow rate in response to the physiological blood pressure.

In embodiments, the control system is configured to receive as an input a pressure value indicative of the physiological blood pressure of a patient, and to adjust the restriction threshold in response to the physiological blood pressure.

In embodiments, the pressure value comprises the Central Venous Pressure (CVP) and/or the Pulmonary Artery Diastolic Pressure (PAD). For ease of reference, CVP characterises the right-side heart function, and PAD characterises the left-side heart function. Under normal physiological conditions, PAD is expected to be higher than CVP.

The pressure value may be measured using established pressure sensors, such as a Swan-Ganz catheter. Such pressure sensors are used routinely during heart surgery. Pressure values may be provided as an input to the controller.

The relationship between the amount of blood in circulation and the pressure values in the vascular system is complex. As the amount of blood in the patient changes, so does the blood pressure in the vascular system and in the heart chambers of the patient. The efficiency of the heart may be described by Starling's Law, which describes the relationship between the stroke volume of the heart and the pre-loaded volume of blood in a heart chamber, which depends on the amount of blood in the vascular system. As a simplified explanation, increasing the amount of blood in circulation results in an increased volume of blood pumped per heartbeat, but only up to a limit. Above the limit, further increasing the amount of blood in circulation decreases the volume of blood pumped per heartbeat. The limit differs among patients but is typically in the region of between 10 to 15 mmHg (1 mmHg=133.322 Pa) for the central venous pressure (CVP) and in the region of 19 to 20 mmHg for the pulmonary artery diastolic pressure (PAD).

For instance, the output flow rate may be maintained higher than the restriction threshold. Initially, only the restriction threshold may be set, e.g., to 2 lpm, whereas the output flow rate may not be adjusted. This means that blood will continue to be supplied towards the patient at a regular, unrestricted level about 5 lpm, but is only allowed to drain at about 2 lpm. This increases the filling rate (i.e., more blood is supplied to the patient than is allowed to leave the patient). As the vascular system is filled, a vascular pressure value (e.g., the central venous pressure, CVP) may also increase. The output flow rate may be maintained above the restriction threshold until the vascular pressure value reaches a pressure threshold. For instance, the filling may be stopped when a pressure threshold of 20 mmHg (PAD) is reached.

Distinguishing between left-side and right-side pressures provides a better control of filling when filling volumes are large relative to the patient. For instance, a translocated volume of 300 ml blood may be a relatively small amount for an adult, and may be considered safe enough as a first-level estimate. In contrast, in paediatric surgery, it may not be considered safe to translocate 300 ml blood. By providing a mechanism that fills the vascular system based on a pressure threshold, a safe volume of blood can be translocated without having to estimate the volume of blood in advance.

When the vascular pressure approximates or reaches the pressure threshold, the difference between the output flow rate and the restriction threshold may be reduced until they match. For instance, the output flow rate may be reduced, and/or the restriction threshold may be increased, until both are at the same level. This will result in the blood supply and drainage being in balance at the pressure threshold.

The filling procedure may be automated by setting a pressure threshold. The controller may modulate the restriction threshold and/or the output flow rate (and thereby, cause the adjustable restriction and/or the pump performance to be adjusted) until the pressure threshold is reached. The procedure may be semi-automated, e.g., by providing an indication to a clinician how, for a set pressure threshold, the restriction and/or the output flow rate should be adjusted, but leaving the actual control over when the adjustment is initiated to the judgment of the clinician.

Furthermore, the control system may be configured to alter the restriction threshold dynamically in response to the pressure value. For instance, while the pressure value is low (or close to zero), the restriction threshold may be very low, allowing the vascular system to be filled quicker. In other words, the ratio of the output flow rate to the restriction threshold may be larger the greater the difference between the pressure value and the pressure threshold. As the pressure in the vascular system starts to increase or change, the restriction threshold may be raised thereby to reduce the restriction, such that ratio of the output flow rate to the restriction threshold decreases. Thereby, the pressure value increases more slowly, which allows more response time to for clinical staff. This provides improved safety while also allowing a high filling rate when this is safe.

The control system may comprise a second pressure threshold or maximum pressure threshold as a safeguard. For instance, once the maximum pressure threshold is reached, the controller may not allow the output flow rate to exceed the restriction threshold. The controller may be configured to increase the restriction threshold to allow more blood to be drained via the venous line.

In embodiments, the control system comprises a processor and software instructions implemented by the processor permitting it to control the adjustable restriction in response to the first flow value.

Likewise, the software instructions may permit the processor to control any of the other components of the control system.

In accordance with a second aspect of the present invention, there is provided a method of restricting the flow rate of blood in a blood line in which blood is permitted to flow from an inlet towards an outlet as defined in claim 14.

The method comprises the steps of: providing a first flow sensor to determine a first flow value indicative of the flow rate in the blood line, providing an adjustable restriction configured to reduce the flow rate in the blood line, and, in response to the first flow value, controlling the adjustable restriction to reduce the flow rate in the blood line to maintain a flow rate that does not exceed below a restriction threshold.

In embodiments, the method comprises determining whether or not the first flow value exceeds the restriction threshold by a pre-determined margin, and adjusting the adjustable restriction to maintain the flow rate below the restriction threshold.

In embodiments, the blood line comprises a venous line for receiving blood into a reservoir. The first flow sensor is used to determine the venous flow rate and the adjustable restriction is configured to maintain the venous flow rate in the venous line.

The restriction threshold may be used to set a venous flow rate, i.e., the flow rate of extracorporeal blood from a patient.

In embodiments, the method is used in a control system for a perfusion system comprising a pump to circulate blood at a pre-determined output flow rate from the reservoir via a main blood line towards an outlet. The method further comprises the steps of: providing a second flow sensor to determine a second flow value indicative of the flow rate in the main blood line, determining whether or not there is an output difference between the second flow value and the pre-determined output flow rate, and adjusting parameters of the pump to reduce the output difference.

The pre-determined output flow rate may be used to set an arterial flow rate, i.e., the flow rate of extracorporeal blood pumped towards the patient.

The second flow sensor may be provided in the form of an arrangement deriving the second flow value from pump parameters or from operational characteristics of the pump.

In embodiments, the method comprises the step of adjusting the pre-determined output flow rate relative to the restriction threshold.

In embodiments, the method comprises the step of synchronously adjusting the pre-determined output flow rate and the restriction threshold.

In embodiments, the method comprises the steps of: monitoring a pressure value indicative of a physiological blood pressure of a patient, determining whether or not the pressure value exceeds a pre-determined pressure threshold, and adjusting the adjustable restriction and/or the parameters of the pump depending on whether or not the pressure value exceeds the pre-determined pressure threshold.

In embodiments, the method comprises, while the pressure value is below the pre-determined pressure threshold, increasing the restriction threshold.

In embodiments, the method comprises, while the pressure value exceeds the pre-determined pressure threshold, reducing the restriction threshold.

In embodiments, the method comprises, while the pressure value is below the pre-determined pressure threshold, adjusting either or both of the restriction threshold and the output flow rate such that the restriction threshold is lower than the output flow rate.

This allows the ratio of the venous flow rate relative to the arterial flow rate to be reduced.

For instance, the arterial flow rate may be increased while maintaining the restriction threshold for the venous line at the same level, to increase the filling rate. This is done to increase the pressure value.

In embodiments, the method comprises, while the pressure value is equal to the pre-determined pressure threshold, maintaining the restriction threshold at a same level as the output flow rate.

In practice, the restriction threshold may be maintained at the same level while the pressure value is at approximately equal to the pre-determined pressure threshold.

This may be achieved by manually setting the restriction threshold and the output flow rate, e.g., by ensuring that both values are set to 2 lpm.

In embodiments, the method comprises, while the pressure value is above the pre-determined pressure threshold, adjusting either or both of the restriction threshold and the output flow rate such that the restriction threshold is higher than the output flow rate.

This allows the ratio of the venous flow rate relative to the arterial flow rate to be increased.

For instance, the arterial flow rate may be reduced while maintaining the restriction threshold for the venous line at the same level, to reduce the filling rate. This is done to reduce the pressure value.

Adjusting the restriction threshold and/or the output flow rate in this manner allows the amount of blood in the vascular system to be increased or decreased, respectively, based on the pressure value (e.g., CVP or PAD).

The pressure value (e.g., CVP or PAD), may change dynamically to a change of the amount of blood in the vascular system. The pressure threshold may be set to take the pressure change into account.

DESCRIPTION OF THE FIGURES

Exemplary embodiments of the invention will now be described with reference to the Figures, in which.

DESCRIPTION

Figure 1:
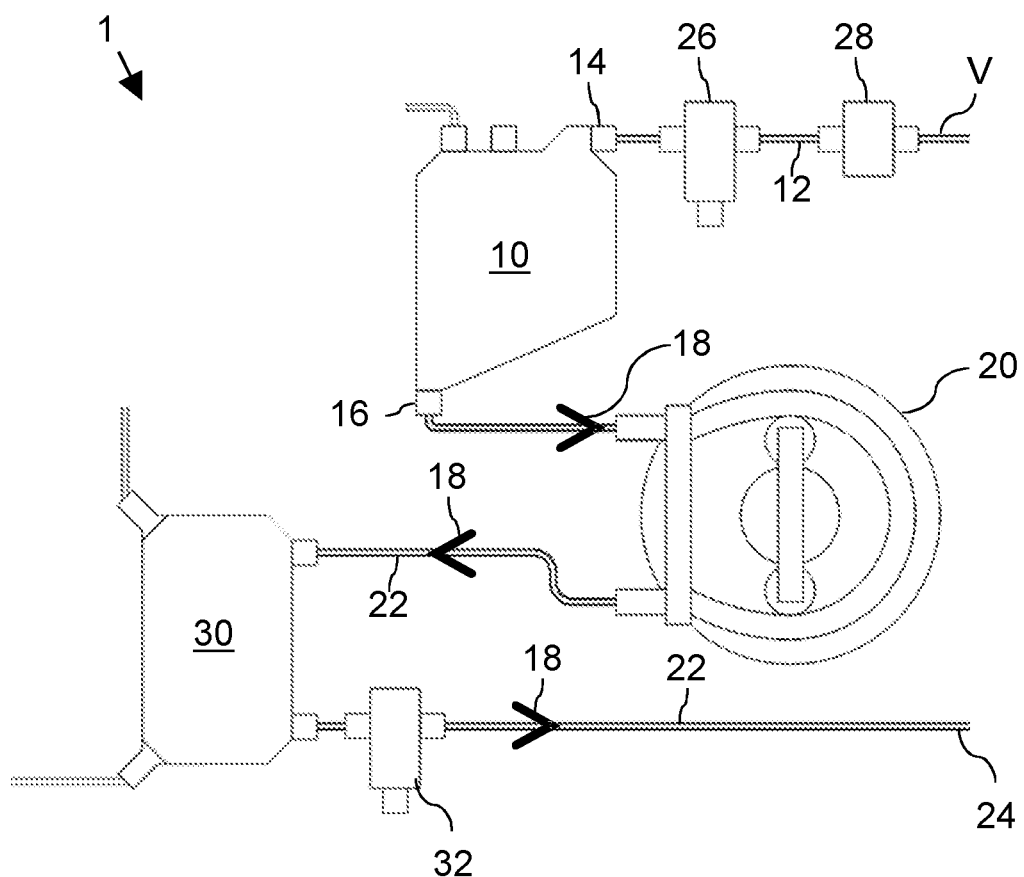
FIG. 1 shows a schematic arrangement of components of a control system to restrict the flow rate in a blood line in accordance with embodiments of the present invention.

FIG. 1 shows, schematically, components of a perfusion system 1. The perfusion system comprises a venous line 12 provided to receive venous blood V from a patient. Via the venous line 12, venous blood is permitted to flow into a reservoir 10 via a reservoir inlet 14. Venous blood is held in the reservoir 10 at atmospheric pressure.

The venous blood may be drawn from the reservoir 10 via a reservoir outlet 16 through the main line 22 of the perfusion system. The blood is pumped by a pump 20, which may be any suitable type of pump, such as a peristaltic pump (e.g., a roller pump) or a centrifugal pump. The pump causes blood to flow through the main line 22 in a direction indicated by arrows 18, via an oxygenator 30 and towards an outlet 24 of the perfusion system 1.

At the outlet 24, the blood is in a condition for administration to a patient. For instance, the blood may have been oxygenated in the oxygenator 30, and the blood will have a flow rate and line pressure sufficient to permit safe administration to a patient. In the absence of losses, it can be assumed that the flow rate and the line pressure are determined by the pump 20. If the pump 20 generates higher throughput, the arterial flow rate is faster. Conversely, if the pump 20 generates lower throughput, the arterial flow rate is slower.

The venous line 12 and the main line 22 may be constituted by flexible tubing. The tubes may have a different length and/or diameter. The tubes may have different strength or flexibility characteristics.

In the venous line 12, the control system comprises a venous flow sensor 26 and a flow-restricting arrangement 28. The venous flow sensor 26 is configured to provide a flow value indicative of the flow rate in the venous line 12, and may be constituted by a mass flow meter. The flow-restricting arrangement 28 may be configured to allow the flow to be restricted gradually. For instance, the flow-restricting arrangement 28 may be constituted by a motorised clamp suitable to squeeze a flexible tube.

In an embodiment, the venous line V constitutes a blood line, the venous line upstream of the flow-restricting arrangement 28 constitutes an inlet of a blood line, the reservoir inlet 14 constitutes an outlet of the blood line, the venous flow sensor 26 constitutes a first flow sensor, and the flow-restricting arrangement 28 constitutes an adjustable restriction.

The motorised clamp is responsive to a controller (controller not shown in FIG. 1) and allows the flow rate in the venous line to be prevented from exceeding a restriction threshold. For instance, the controller may issue a control signal to the motorised clamp to squeeze the venous line 12 until the flow rate, as determined by the flow sensor 26, no longer exceeds the restriction threshold.

Due to the closed loop control, it is not necessary to know by how much the tube was squeezed, or which type of equipment was used, in order to maintain the restriction threshold.

Partially clamping the flexible tube to a sufficient extent allows the flow rate in the venous line 12 to be restricted. By gradually opening the clamp, the degree of restriction of the flow rate in the venous line 12 can be reduced until there is no flow rate restriction by the flow-restricting arrangement 28.

Downstream of the reservoir 10, (in FIG. 1 also downstream of the oxygenator 30), the perfusion system is provided with a main flow sensor 32. The main flow sensor 32 allows the flow rate of the blood provided towards the patient to be measured. The flow rate towards the patient may be regarded as output flow rate. The flow sensor 32 is configured to provide a second flow value indicative of the flow rate in the main blood line, i.e., of the flow rate through the outlet 24.

A controller (not shown in FIG. 1) is configured to receive as an input a restriction threshold to indicate the maximum flow rate through the venous line 12. For instance, the restriction threshold may be set via an interface. The restriction threshold may be set as an absolute value (e.g., 2 lpm) or as a relative value (e.g., half of the current flow). The current flow rate may be determined by the venous flow sensor 26 or by the main flow sensor 32. For instance, the restriction threshold may be set to half the second flow value.

The controller is configured to receive a venous flow value indicative of the venous flow rate, as determined by the flow sensor 26. The controller comprises decision logic to determine whether or not the venous flow rate exceeds the restriction threshold. If the venous flow value does not exceed the set restriction threshold, the flow-restricting arrangement 26 is not actuated. If the venous flow value exceeds the set restriction threshold, the controller may issue a control signal to the flow-restricting arrangement 28 to increase the flow restriction until the venous flow rate no longer exceeds the restriction threshold.

After the flow-restricting arrangement has been set, the controller continues to monitor the venous flow as determined by the flow sensor 26. If, for any reason, the flow value exceeds the restriction threshold despite a previously appropriate restriction setting, the controller issues a control signal to the flow-restricting arrangement 28 to adjust the restriction threshold.

In one embodiment, the controller is configured to operate the pump 20 to maintain a pre-determined output flow rate. The second flow value may be derived from operational parameters of the pump 20. The second flow value may be determined by the flow sensor 32.

The pre-determined output flow rate and the restriction threshold may each be set independently, e.g., in absolute values, via an input interface.

The controller may be configured to adjust the output flow rate through the outlet 24 relative to the restriction threshold in the venous line 12.

For instance, the restriction threshold and the pre-determined output flow rate may be matched. The venous flow threshold may be set to 2 lpm, and venous blood can be expected not to flow into the reservoir 10 faster than at a rate of 2 lpm. The controller may adjust the operation of the pump 20 such that the flow rate through the outlet, as measured by the main flow sensor 32, is not more than 2 lpm.

In the venous line 12, the actual venous flow rate is monitored by the first flow sensor 26. If, for any reason, the actual venous flow rate exceeds the threshold of 2 lpm, the controller is configured to respond by increasing the flow restriction, until the venous flow rate is at, or below, 2 lpm.

If the pre-determined output flow rate and the restriction threshold are set independently, a change of the pre-determined output flow rate will not affect the restriction threshold.

While the controller is set to match the main flow rate and the venous flow rate, the pump parameters may be changed according to the venous flow threshold. For instance, the venous flow restriction may be reduced by setting the venous flow threshold from 2 lpm to 3 lpm. The controller may increase the pump speed until the main flow rate is 3 lpm. Likewise, the venous flow restriction may be increased (the restriction threshold may be lowered), e.g., from 2 lpm to 1 lpm. The controller may reduce the pump speed to reduce the main flow rate to 1 lpm.

The restriction threshold may be below or above the pre-determined output flow rate. This provides a control over the blood supply during the different end phases of extracorporeal perfusion.

To initiate the end of extracorporeal perfusion support, the restriction threshold may be reduced to restrict the venous flow, e.g., to 2 lpm. At this stage, the output flow rate as determined by the pump may continue to be governed by normal perfusion requirements. Such requirements may include cardiac index values and venous saturation. The output flow rate may be in the region of 5 lpm. As the output flow rate exceeds the venous flow, this results in a gradual filling of the vascular system.

When the vascular system is filled to a sufficient extent (this may be determined by a physiological blood pressure), the restriction threshold may be maintained and the pre-determined output flow rate may be set to match the restriction threshold. The output flow rate is no longer governed exclusively by normal perfusion requirements. For instance, the pre-determined output flow rate and the restriction threshold may be adjusted to such that the CVP is close to, but not exceeding 15 mmHg, and/or such that the PAD is close to, but not exceeding 20 mmHg.

The restriction threshold of the venous line and the pre-determined output flow rate of the main line may be adjusted synchronously. If the heart performs satisfactorily at a perfusion flow rate of 2 lpm, the restriction threshold and the pre-determined output flow rate may be reduced further, e.g., from 2 lpm to 1 lpm, to further encourage heart activity. This may affect the pressure levels, such as CVP and/or PAD. If a pressure level is too low, the pre-determined output flow rate may be temporarily increased relative to the restriction threshold in order to increase the CVP or PAD value. If a pressure level is too high, the output flow rate may be temporarily decreased, and/or the restriction threshold may be partially lifted.

The restriction threshold and the pre-determined output flow rate may be adjusted independently. For instance, a clinician may wish to adjust these thresholds manually according to other blood values, such as venous oxygen saturation.

If heart performance at the reduced output flow rate is insufficient, extracorporeal perfusion may be resumed by increasing the output flow rate and/or by lifting the restriction threshold.

If the heart performs well with a reduced extracorporeal perfusion support, extracorporeal perfusion support may be further reduced, by setting a the pre-determined output flow rate to a lower level, until a decision can be made to completely cease extracorporeal perfusion and to let the heart take over circulation.

Figure 2:
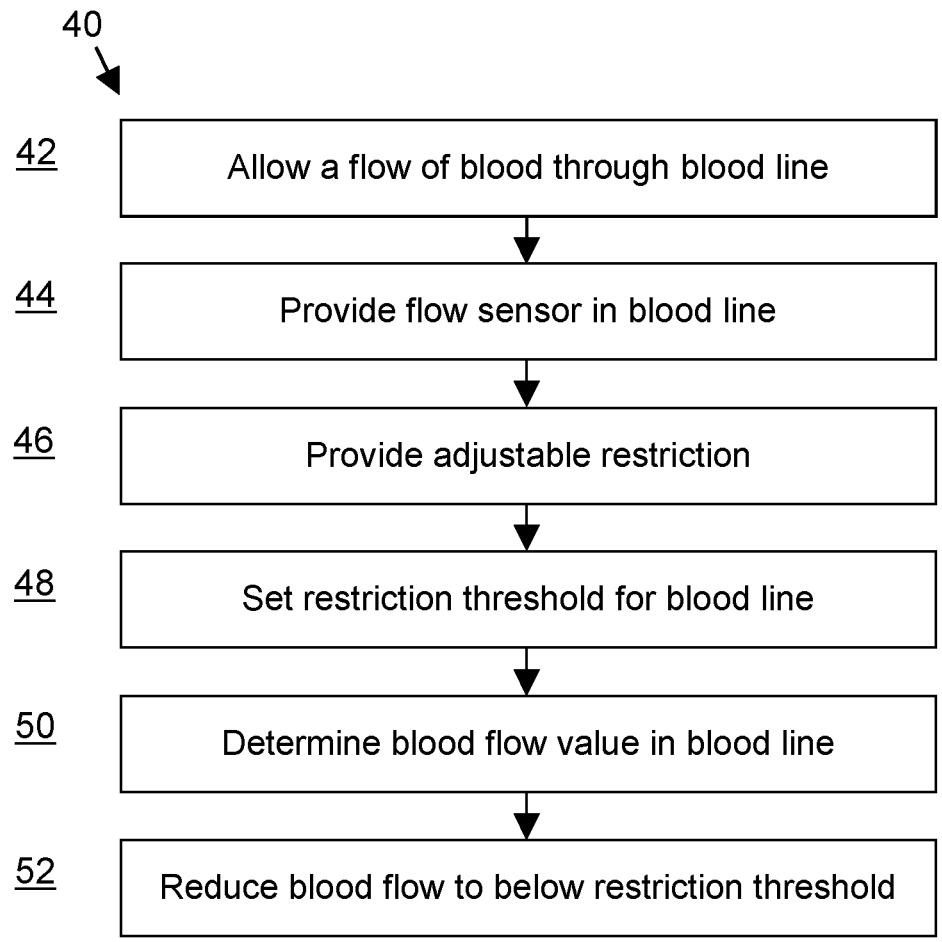
FIG. 2 shows steps of an exemplary sequence of method steps of a method for restricting the flow rate in a blood line in accordance with embodiments of the present invention.

In FIG. 2, steps of a control method 40 or restricting the flow rate in a blood line, such as a venous line, are shown. In step 42, blood is permitted to flow through a blood line. In step 44, a blood flow sensor is provided in the blood line, to provide a blood flow value indicative of the flow rate in the blood line. In step 46, an adjustable restriction is provided to allow the flow through the blood line to be reduced. In step 48, a restriction threshold is set. The restriction threshold may be regarded as a maximum blood flow rate level. In step 50, the blood flow value (e.g., of venous blood) is determined by the blood flow sensor. In step 52, the blood flow is reduced, using the adjustable restriction, to below the restriction threshold. The restriction threshold remains responsive to the flow rate. I.e., if a blood flow value is determined to be higher than the restriction threshold, the adjustable restriction is re-adjusted to limit the flow rate to the restriction threshold.

Threshold values described herein, such as the restriction threshold, the output flow rate, and pressure thresholds, may include a margin to avoid an overshooting response.

The invention claimed is:

1. A control system for use in a perfusion system during an end phase of perfusion support, the perfusion system having a pump to circulate blood from a reservoir via a main blood line towards an outlet of the main blood line, the control system configured to restrict the flow rate of blood in a venous line in which blood is permitted to flow from an inlet towards an outlet of the venous line, wherein the control system comprises:
a first flow sensor configured to determine a first flow value indicative of the flow rate in the venous line;
a second flow sensor configured to determine a second flow value indicative of the flow rate in the main blood line;
a controller configured to process the first flow value and the second flow value, and to modulate operation of the pump to maintain the throughput towards the outlet of the main blood line at a pre-determined flow rate; and
an adjustable restriction responsive to the controller, wherein the adjustable restriction is configured to reduce the flow rate in the venous line to maintain a flow rate that does not exceed a restriction threshold, and wherein
the controller is further configured to
receive, as an input, a pressure value indicative of the physiological blood pressure of a patient,
determine a difference between the second flow value and the pre-determined output flow rate, and to adjust pump parameters to reduce the difference,
initially, maintain the pre-determined output flow rate above the restriction threshold, and
subsequently, adjust the pre-determined output flow rate and/or the restriction threshold in response to a change in the pressure value.

2. The control system in accordance with claim 1, further configured to determine if the first flow value exceeds the restriction threshold by a pre-determined margin, and configured to effect an adjustment of the adjustable restriction to maintain the flow rate below the restriction threshold.

3. The control system according to claim 1, wherein the adjustable restriction comprises a gradually actuatable occlusive device.

4. The control system according to claim 1, wherein the control system is configured to allow the restriction threshold and the pre-determined output flow rate to be set independently.

5. The control system according to claim 1, wherein the controller is configured to adjust the pre-determined output flow rate relative to the restriction threshold.

6. The control system according to claim 5, wherein the controller is configured to maintain the pre-determined output flow rate at a level selected from the group consisting of: above the restriction threshold, at the restriction threshold, and below the restriction threshold.

7. The control system according to claim 1, wherein the pressure value comprises a value selected from the group consisting of: the Central Venous Pressure (CVP) and the Pulmonary Artery Diastolic Pressure (PAD).

8. The control system according to claim 1, further comprising a processor and software instructions implemented by the processor permitting it to control the adjustable restriction in response to the first flow value.

9. The control system in accordance with claim 1, wherein the second flow sensor is provided in the form of an arrangement deriving the second flow value from pump parameters or from operational characteristics of the pump.

10. A method of restricting the flow rate of blood in a perfusion system during an end phase of perfusion support, the perfusion system comprising a pump to circulate blood from a reservoir via a main blood line towards an outlet of the main blood line, the method being for restricting the flow rate of blood in a venous-line in which blood is permitted to flow from an inlet towards an outlet of the venous line, the method comprising:
determining, by a first flow sensor, a first flow value indicative of the flow rate in the venous line;
in response to the first flow value, controlling an adjustable restriction to reduce the flow rate in the venous line to maintain a flow rate that does not exceed a restriction threshold;
determining, by a second flow sensor, a second flow value indicative of the flow rate in the main blood line;
controlling operation of the pump to maintain throughput towards the outlet of the main blood line at a pre-determined flow rate;
monitoring a pressure value indicative of the physiological blood pressure of a patient;
determining if there is an output difference between the second flow value and the pre-determined output flow rate;
adjusting parameters of the pump to reduce the output difference;

initially, maintaining the pre-determined output flow rate above the restriction threshold;

determining if the physiological blood pressure exceeds a pressure threshold; and subsequently, adjusting the pre-determined output flow rate and/or the restriction threshold in response to a change in the pressure value.

11. The method in accordance with claim 10, further comprising:

determining if the first flow value exceeds the restriction threshold by a pre-determined margin, and adjusting the adjustable restriction to maintain the flow rate below the restriction threshold.

12. The method according to claim 10, further comprising adjusting the pre-determined output flow rate relative to the restriction threshold.

13. The method according to claim 10, further comprising synchronously adjusting the pre-determined output flow rate and the restriction threshold.

14. The method in accordance with claim 10, comprising, while the pressure value is below the pre-determined pressure threshold, increasing the restriction threshold.

15. The method in accordance with claim 10, comprising, while the pressure value exceeds the pre-determined pressure threshold, reducing the restriction threshold.

* * * * *